US011478652B2

(12) United States Patent
Lim et al.

(10) Patent No.: US 11,478,652 B2
(45) Date of Patent: Oct. 25, 2022

(54) IMPLANTABLE MEDICAL DEVICE WITH MODULAR INJECTION MOLDED HEADER ASSEMBLY AND RELATED METHODS OF MANUFACTURE

(71) Applicant: PACESETTER, INC., Sylmar, CA (US)

(72) Inventors: Wisit Lim, Santa Clarita, CA (US); Reza Imani, Moorpark, CA (US); Brett Villavicencio, Valencia, CA (US); Mitch Goodman, Santa Clarita, CA (US)

(73) Assignee: Pacesetter Inc., Sylmar, CA (US)

( * ) Notice: Subject to any disclaimer, the term of this patent is extended or adjusted under 35 U.S.C. 154(b) by 322 days.

(21) Appl. No.: 15/073,294

(22) Filed: Mar. 17, 2016

(65) Prior Publication Data
US 2017/0266451 A1      Sep. 21, 2017

(51) Int. Cl.
*A61N 1/375* (2006.01)
*A61N 1/362* (2006.01)
*A61N 1/372* (2006.01)

(52) U.S. Cl.
CPC ........... *A61N 1/3754* (2013.01); *A61N 1/362* (2013.01); *A61N 1/37229* (2013.01); *A61N 1/37512* (2017.08)

(58) Field of Classification Search
None
See application file for complete search history.

(56) References Cited

U.S. PATENT DOCUMENTS

| | | | | |
|---|---|---|---|---|
| 5,144,946 A | * | 9/1992 | Weinberg | A61N 1/3758 607/2 |
| 7,239,916 B2 | * | 7/2007 | Thompson | A61N 1/37252 607/119 |
| 7,447,533 B1 | * | 11/2008 | Fang | A61B 5/0402 600/310 |
| 7,630,768 B1 | * | 12/2009 | Coffed | A61N 1/3752 607/37 |
| 8,065,009 B2 | | 11/2011 | Biggs | |
| 9,065,224 B2 | † | 6/2015 | Marzano | |
| 9,692,173 B2 | † | 6/2017 | Marzano | |
| 2003/0163171 A1 | * | 8/2003 | Kast | A61N 1/3752 607/36 |
| 2009/0264943 A1 | * | 10/2009 | Barker | A61N 1/3752 607/2 |
| 2010/0274313 A1 | * | 10/2010 | Boling | A61N 1/0546 607/46 |
| 2012/0016444 A1 | * | 1/2012 | Koester | A61N 1/3754 607/57 |
| 2012/0090161 A1 | | 4/2012 | Biggs, Jr. et al. | |
| 2015/0077050 A1 | * | 3/2015 | Van Funderburk | H02J 5/005 320/108 |
| 2017/0291034 A1 | † | 10/2017 | Marzano | |

* cited by examiner
† cited by third party

*Primary Examiner* — Jennifer Pitrak McDonald
*Assistant Examiner* — Elizabeth K So
(74) *Attorney, Agent, or Firm* — The Small Patent Law Group LLC; Dean D. Small (57) ABSTRACT

Disclosed herein is an implantable electronic device. In one embodiment, the device has a modular header-feedthru assembly and a housing. The modular header-feedthru assembly has a conductor assembly, a feedthru coupled to the conductor assembly, and a polymer header that is injected molded about the conductor assembly and at least a portion of the feedthru. The housing is welded to the feedthru.

22 Claims, 10 Drawing Sheets

IMPLANTABLE MEDICAL DEVICE WITH MODULAR INJECTION MOLDED HEADER ASSEMBLY AND RELATED METHODS OF MANUFACTURE

FIELD OF THE INVENTION

Aspects of the present invention relate to medical apparatus and methods. More specifically, the present invention relates to systems and methods for manufacturing a header assembly of an implantable electronic device such as an implantable pulse generator or implantable cardiac monitor.

BACKGROUND OF THE INVENTION

Implantable electronic devices (IEDs) include pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems. These IPGs commonly include a housing, feedthrus, and a connector assembly that is enclosed in a header and includes many internal electrically conductive components such as, for example, wires, ribbon, antennas, blocks, rings, etc. Electrical stimulation originating in the housing is led to the connector assembly through feedthrus. The connector assembly serves to transmit electrical signals out of the IPG and to a lead electrically connected to the connector assembly, the lead transmitting electrical signals between the IPG and patient tissue.

Other IEDs include implantable cardiac monitors (ICMs). ICMs also employ a housing, feedthrus, a header, and internal electrically conductive components of the header, such as, for example, antennas and sensing electrodes. ICMs are used to monitor heart function or other electrical signals, but do not administer electrotherapy.

Conventional processes for fabricating a header of an IED employ epoxy casting the header about the header's electrically conductor components and to the device after the feedthru has been welded to the device case. The epoxy casting process is a labor intensive process that requires significant secondary operations such as, for example, buffing, sanding and cleaning of the header and the housing. Such secondary processes require a dedicated wet room that is outside the cleanroom used in the assembly of the header to the housing.

There is a need in the art for an IED that is less expensive and labor intensive to manufacture.

BRIEF SUMMARY OF THE INVENTION

Disclosed herein is an implantable electronic device. In one embodiment, the device includes a modular header-feedthru assembly and housing. The modular header-feedthru assembly includes a conductor assembly, a feedthru coupled to the conductor assembly, and a polymer header that was injected molded about the conductor assembly and at least a portion of the feedthru. The housing is welded to the feedthru.

The at least a portion of the feedthru may include a groove and the polymer header may fully occupy the groove in anchoring the polymer header to the feedthru. The groove may extend in a recessed manner horizontally and circumferentially about a base of the feedthru. The groove may have a recess depth of between approximately 0.01" and approximately 0.03", and a recess height of between approximately 0.01" and approximately 0.03".

The housing may enclose at least one of a battery or a hybrid. The welding between the housing and the feedthru may form a hermetic seal between the housing and the feedthru.

The feedthru may include a feedthru terminal that is in electrical communication with the conductor assembly and extends from the feedthru into a female electrical receptacle supported by the housing to make electrical contact with the female electrical receptacle. The female electrical receptacle may be in electrical communication with electronic components contained in the housing.

The feedthru terminal may be plugged into the female electrical receptacle. The female electrical receptacle may include a biasing member that biases against the feedthru terminal. The biasing member may include a funnel portion.

The polymer header may include a thermoplastic. The polymer header may include Tecothane and/or Pallathane.

The implantable electronic device may be an implantable cardiac monitor. The conductor assembly may include an electrode plate and a BLE antenna. The electrode plate may include an electrode surface in the form of a generally continuous flat surface. The electrode plate may include an electrode surface including at least one of bumps or recesses.

The implantable electronic device may be an implantable pulse generator. The conductor assembly may be in the form of a connector assembly including a ring block, a tip block, and/or an antenna. The implantable electronic device may also include an implantable medical lead configured to electrically couple with the implantable pulse generator.

Also disclosed herein is a method of manufacturing an implantable electronic device. In one embodiment, the method includes: direct injection mold a polymer material about a conductor assembly and an upper portion of a feedthru base to form a modular header-feedthru assembly; mate a bottom portion of the feedthru base with a top portion of a housing of the implantable electronic device; and weld the bottom portion of the feedthru base to the top portion of the housing.

The housing may enclose at least one of a battery or a hybrid. The welding between the top portion of the housing and the bottom portion of the feedthru base may form a hermetic seal between the housing and the feedthru.

The method may further include plugging a feedthru terminal into a female electrical receptacle to make electrical contact with the female electrical receptacle. The feedthru may include the feedthru terminal, which is in electrical communication with the conductor assembly. The feedthru terminal may extend from the feedthru into the female electrical receptacle, which may be supported by a hybrid that is supported by the housing such that it can be said that the female receptacle is operably coupled to the housing. The female electrical receptacle may be in electrical communication with electronic components contained in the housing.

The polymer material may include a thermoplastic. The polymer material may include at least one of Tecothane or Pallathane.

The implantable electronic device manufactured via the method may be an implantable cardiac monitor. The conductor assembly may include an electrode plate and a BLE antenna.

The implantable electronic device manufactured via the method may be an implantable pulse generator. The conductor assembly may be in the form of a connector assembly including at least one of a ring block, a tip block, or an antenna.

The feedthru may include a groove and the polymer material may be caused to fully occupy the groove in anchoring the polymer material to the feedthru. The groove may extend in a recessed manner horizontally and circumferentially about the feedthru base. The groove may have a recess depth of between approximately 0.01" and approximately 0.03", and a recess height of between approximately 0.01" and approximately 0.03".

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

Implementations of the present disclosure involve an implantable electronic device (IED) 20 such as an implantable cardiac monitor (ICM) or an implantable pulse generator (IPG). The IPG administers electrotherapy or other neurostimulation via an implantable lead having a lead connector end on a proximal end of the implantable lead. The IPG includes a housing or can and a connector assembly enclosed in a header to form a header connector assembly that is coupled to the housing or can. The header connector assembly has at least one lead connector receiving bore or receptacle that includes electrical contacts of the connector assembly that make electrical contact with corresponding electrical terminals on the lead connector end on the proximal end of the implantable lead when the lead connector end is plugged into or otherwise received in the lead connector receiving bore or receptacle. Via the electrical connection between the corresponding electrical terminals of the lead connector end and the electrical contacts of the lead connector receiving bore, electrical signals can be administered from the IPG and through the lead to patient tissue. Similarly, but in reverse, electrical signals originating in patient tissue can travel via the lead to the IPG to be sensed at the IPG.

The ICM is similar to the IPG in that it also includes a housing or can and a header. However, unlike the IPG, the ICM does not attach to leads and the ICM simply monitors electrical signals and does not administer therapy.

The implantable electronic device configurations and methods of assembly disclosed herein are advantageous for at least the reason that they save manufacturing costs. Specifically, the implantable electronic devices disclosed herein employ an advantageous modular assembly of an IED 20 that is able to take advantage of direct injection molding for the manufacture of a modular header-feedthru assembly 106, which can then be plugged into the device housing 24 and welded thereto. The resulting IED 20 are advantageous in that they have a robust configuration that has less associated manufacturing costs than those devices known in the art.

Before beginning a detailed discussion of the modular aspects of the IED 20 and the corresponding methods of manufacture, a general discussion is first given regarding features of a lead connector end at the proximal end of an implantable medical lead followed by a general discussion of the features of an IPG 20. A general discussion is then given regarding the features of an ICM 20, followed immediately thereafter by a detailed discussion of the modular aspects of the devices 20 and the related methods of manufacture.

A. Overview of a Lead Connector End and IPG

Figure 1:
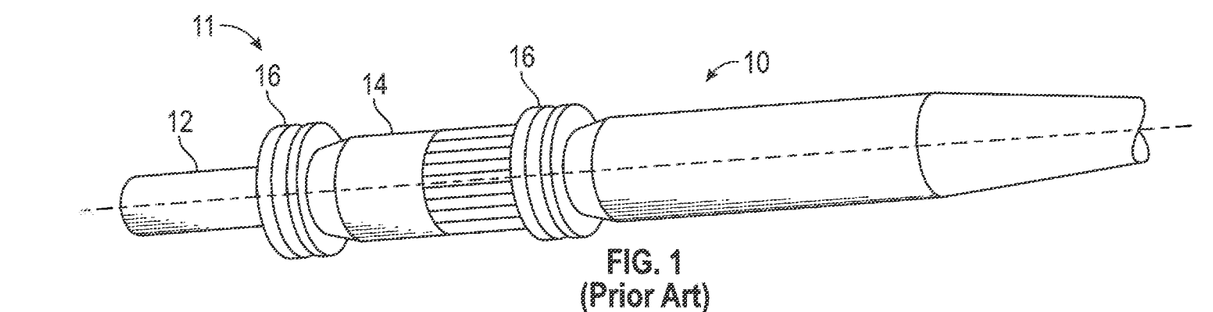
FIG. 1 is an isometric view of a proximal end portion (i.e., lead connector end) of a conventional transvenous bipolar pacing lead.

FIG. 1 shows a proximal end portion 10 of a conventional transvenous, bipolar pacing lead, but is generally representative of any type of implantable lead whether in the cardiac, pain management or other medical treatment space. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing. It should be understood, however, that other lead designs may be used, for example, multipolar leads have proximal ends portions that are bifurcated, trifurcated or have other branched configurations. While the lead whose proximal end is shown in FIG. 1 is of the bipolar variety, there are unipolar leads that carry but a single electrode, and multipolar leads that have more than two electrodes.

As is well known in the art, bipolar coaxial leads typically consists of a tubular housing of a biocompatible, biostable insulating material containing an inner multifilar conductor coil that is surrounded by an inner insulating tube. The inner conductor coil is connected to a tip electrode on the distal end of the lead. The inner insulating tube is surrounded by a separate, outer multifilar conductor coil that is also enclosed within the tubular housing. The outer conductor coil is connected to an anodal ring electrode along the distal end portion of the lead. The inner insulation is intended to electrically isolate the two conductor coils preventing any internal electrical short circuit, while the housing protects the entire lead from the intrusion of body fluids. These insulating materials are typically either silicone rubber or polyurethane. More recently, there have been introduced bipolar leads in which multifilar cable conductors contained within multilumen housings are substituted for the conductor coils in order to reduce even further the overall diameter of the lead.

The proximal lead end portion 10 shown in FIG. 1 includes a lead connector end 11 that conforms to the IS-1 standard, comprising a pair of coaxial spaced-apart electrical terminals including a tip terminal 12 and a ring terminal 14. The tip terminal 12 is electrically connected by means of the inner conductor coil to the tip electrode at the distal end of the lead, while the ring terminal 14 is electrically connected to the anodal ring electrode by means of the outer conductor coil. The tip and ring terminals of the lead connector end may each be engaged by a conductive garter spring contact or other resilient electrical contact element in a corresponding lead connector receiving bore of the header, the resilient electrical contact element being carried by a connector assembly enclosed in the header as described below. The lead connector end 11 on the proximal lead end portion 10 further comprises spaced-apart pairs of seal rings 16 for abutting against in a fluid-sealing manner the inner circumferential surface of the lead connector receiving bore of the header, thereby preventing body fluids from reaching the electrical terminals and contacts when the lead connector end 11 is plugged into the corresponding lead connector receiving bore. With the lead connector end 11 of the lead inserted in the lead connector receiving bore of the header and connector assembly, the tip and ring terminals 12 and 14 are electrically coupled via the contacts of the connector assembly and a feedthru to the electronic circuits within the hermetically sealed housing of the IPG (e.g., cardiac pacemaker, ICD, or other implantable tissue stimulation and/or sensing device such as those used in pain management, etc.).

Figure 2:
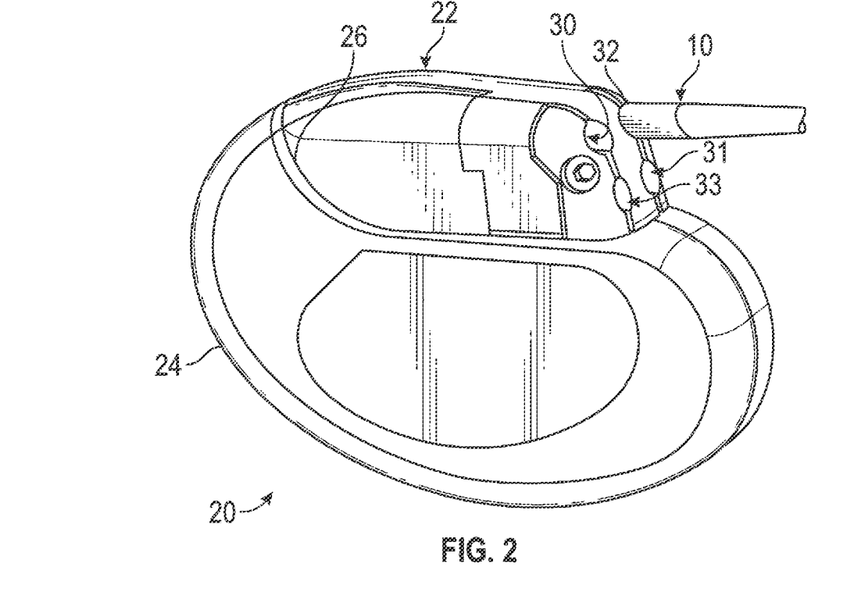
FIG. 2 is an isometric view of a cardiac pacemaker/defibrillator unit (i.e., implantable pulse generator (IPG)) incorporating connector junctions or terminals for communication with one or more electrodes.

FIG. 2 shows a multi-site or multi-chamber cardiac pacemaker/defibrillator unit that is generally representative of any type of IPG 20 incorporating a header connector assembly 22 coupled to a housing 24. The header connector assembly 22 includes a header 40 enclosing a connector assembly 42, both of which are depicted respectively in FIGS. 3, 4A and 4B discussed below. The IPG 20 is of a conventional design, including a hermetically sealed housing 24, which is also known as a can or casing, The housing 24 encloses the electronic components (e.g., battery, hybrid, etc.) of the IPG 20 with the header connector assembly 22 mounted along a top surface 26 of the housing 24.

FIG. 2 illustrates that, in some embodiments, the header connector assembly 22 may include four or more lead connector receiving bores or receptacles 30, 31, 32 and 33 for receiving the lead connector ends of four implantable leads. FIG. 2 also shows the proximal end portion 10 of a lead, wherein the lead connector end on the proximal end portion 10 of the lead is received in a corresponding receptacle 32. In other embodiments, the header connector assembly 22 includes two receptacles comprising a single pair of receptacles (i.e., receptacles 30 and 33) for receiving the proximal ends of leads such as, for example, conventional bipolar leads and/or conventional cardioverting and/or defibrillating leads.

Figure 3:
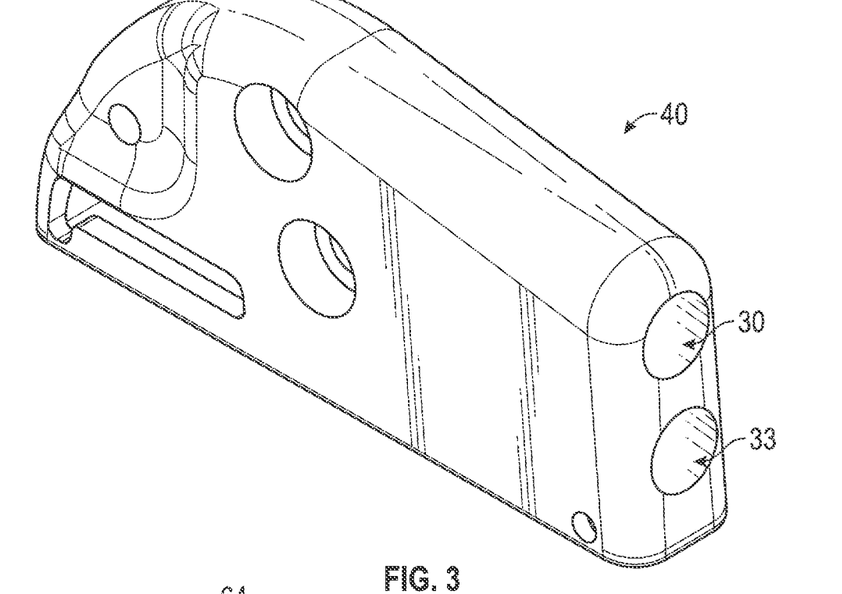
FIG. 3 is an isometric view of a representative header.
Figure 4A:
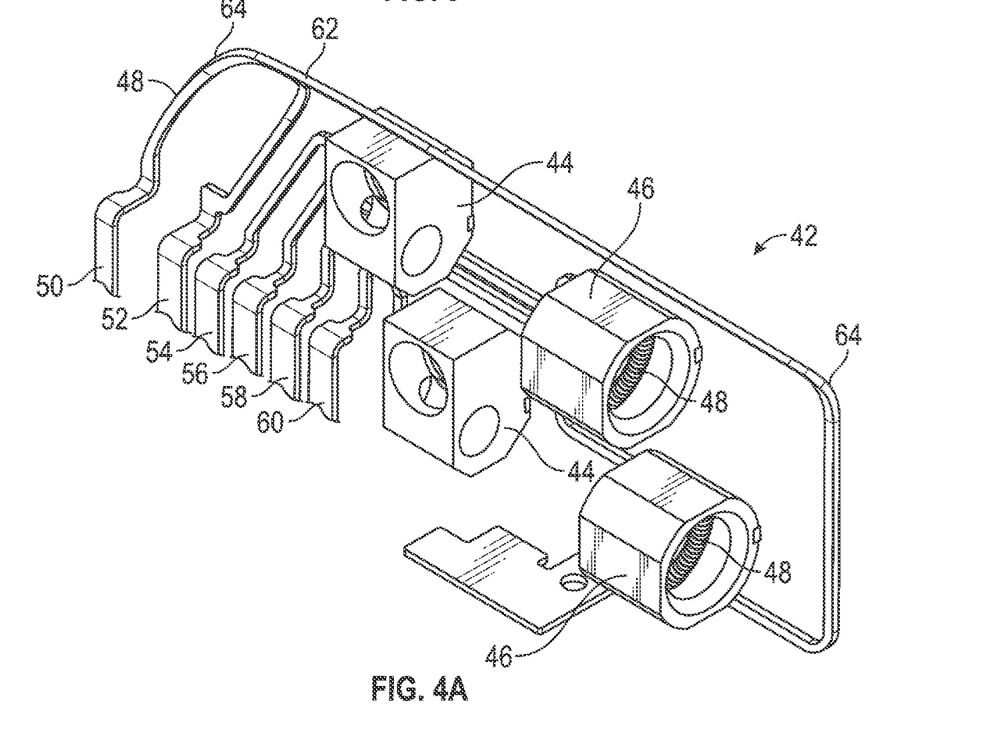
FIGS. 4A and 4B are opposite isometric views of a representative connector assembly used with the header of FIG. 3 to form a header connector assembly.
Figure 4B:
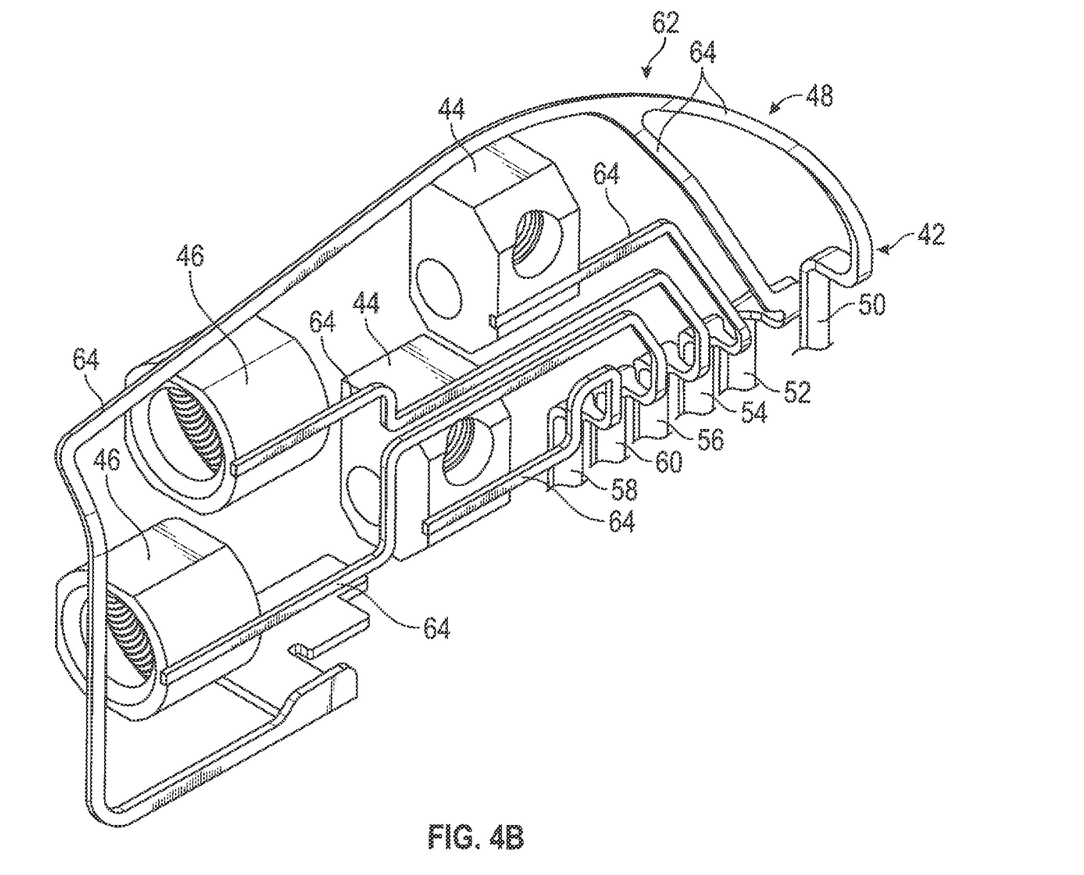

FIG. 3 is an isometric view of a representative header 40, and FIGS. 4A and 4B are opposite isometric views of a representative connector assembly 42. Unlike the header connector assembly 22 of FIG. 2, the header 40 of FIG. 3 only has a single pair of receptacles 30 and 33. However, in other embodiments, the header 40 of FIG. 3 may have two or more pairs of receptacles similar to the embodiment of FIG. 2.

As illustrated in FIGS. 4A and 4B, the connector assembly 42 includes tip blocks 44 and ring blocks 46. The ring blocks 46 include spring contacts 48. Each electrical block 44 and 46 of the connector assembly 42 serves as an electrical contact of the connector assembly 42. Thus, as can be understood from FIGS. 1-4B, each tip block 44 is configured to receive and make electrical contact with the tip terminal 12 of a lead connector end 11 received in the corresponding receptacle 30, 33 of the header 40. Similarly, each ring block 46 is configured to receive and make electrical contact with the ring terminal 14 of a lead connector end 11 received in the corresponding receptacle 30, 33 of the header 40. While the connector assembly 42 of FIGS. 4A and 4B is of an IS-1 configuration, other configurations (e.g., IS-4, etc.) are used in other embodiments. While the connector assembly 42 of FIGS. 4A and 4B only depicts two pairs of blocks 44, 46, in other embodiments where the header includes more than a single pair of receptacles 30, 33 (e.g., two pairs of receptacles 30, 31, 32, 33 as indicated in FIG. 2), the connector assembly 42 will have a four pairs of blocks 44, 46.

As shown in FIGS. 4A and 4B, the connector assembly 42 also includes a host of electrically conductive components including an antenna 48, an RF anchor tab 50, an RF pin tab 52, an A-tip tab 54, an A-ring tab 56, an RV-ring tab 58, an RV-tip tab 60, and a ribbon carrier 62 and other conductors 64 that extend between the various tabs and their respective electrical contacts of the connector assembly or other components thereof. In other words, as can be understood from FIGS. 4A and 4B, electrical conductor elements (e.g., wires, traces. or other electrical conductors) 64 extend between the electrical blocks 44, 46 and the respective tabs 50, 52, 54, 56, 58 and 60, Also, such conductor elements 64 may form the antenna 48 and the ribbon carrier 62. The connector assembly 42 is manufactured of materials and via methods known in the industry.

The various tabs are welded to corresponding terminals 100 of a feedthru 102 similar to that discussed below with respect to FIGS. 9A and 9B. As discussed in detail below, once the header assembly 22 is completed such that the header 40 is injected molded about the electrically conductive components (e.g., in the case of an IPG 20, the electrically conductive components of the connector assembly 42) and to the feedthru 102 to form a resulting modular header-feedthru assembly 106 similar to those discussed below with respect to FIGS. 6A-6E, the feedthru terminals 100 are plugged into electrical receptacles 104 located in the housing 24 of the IPG 20 similar to that discussed below with respect to FIGS. 10 and 11. As a result, the feedthru terminals 100 extend from circuitry of the IPG 20 contained in the housing 24 of the IPG 20 to the electrically conductive components of the connector assembly 42.

As can be understood from the preceding discussion and as provided in greater detail below, the header-feedthru assembly 106 forms a first module that is plugged into electrical receptacles 104 of the housing 24, which forms a second module. The feedthru 102 of the header-feedthru assembly 106 is welded to the housing 24 to complete the assembly of the IPG 20 as it generally appears in FIG. 2.

These concepts discussed above with respect to an IPG 20 will now be discussed with respect to an ICM 20.

B. Overview of an ICM

Figure 5:
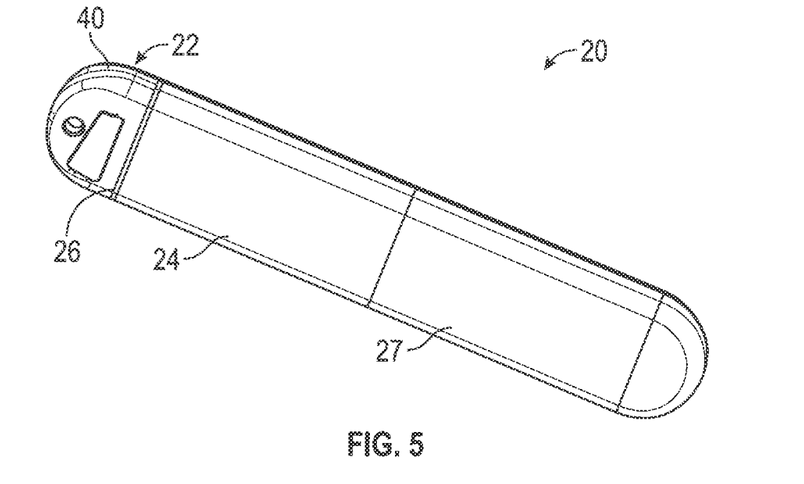
FIG. 5 is an isometric view of an ICM incorporating a header assembly coupled to a housing.

FIG. 5 is an isometric view of an ICM 20 incorporating a header assembly 22 coupled to a housing 24. The ICM 20 is of a conventional design, including a hermetically sealed housing 24, which is also known as a can or casing. The housing 24 encloses the electronic components of the ICM 20 with the header assembly 22 mounted along a top surface 26 of the housing 24. Depending on the embodiment, the casing may enclose the battery, or, as depicted in FIG. 5, the battery case 27 may be welded to the housing at seam A. The battery is electrically connected to the hybrid contained in the housing.

FIGS. 6A-6E are isometric views of modular header-feedthru assemblies 106 incorporating the header assembly 22 of an ICM 20 along with a feedthru 102. The modular header-feedthru assembly of FIGS. 6A and 6B employs an electrode plate 108 of a first configuration, and the modular header-feedthru assembly of FIGS. 6C-6E employs an electrode plate 108 of a second configuration.

As can be understood from FIGS. 6A-6E, the header assembly 22 includes the conductor assembly 42, which includes an electrode plate 108 and a Bluetooth low energy ("BLE") antenna 110. The electrode plate 108 is welded or otherwise electrically coupled to its respective feedthru terminal 100. Similarly, the BLE antenna 110 is welded or otherwise electrically coupled to its respective feedthru terminal 100.

Figure 6A:
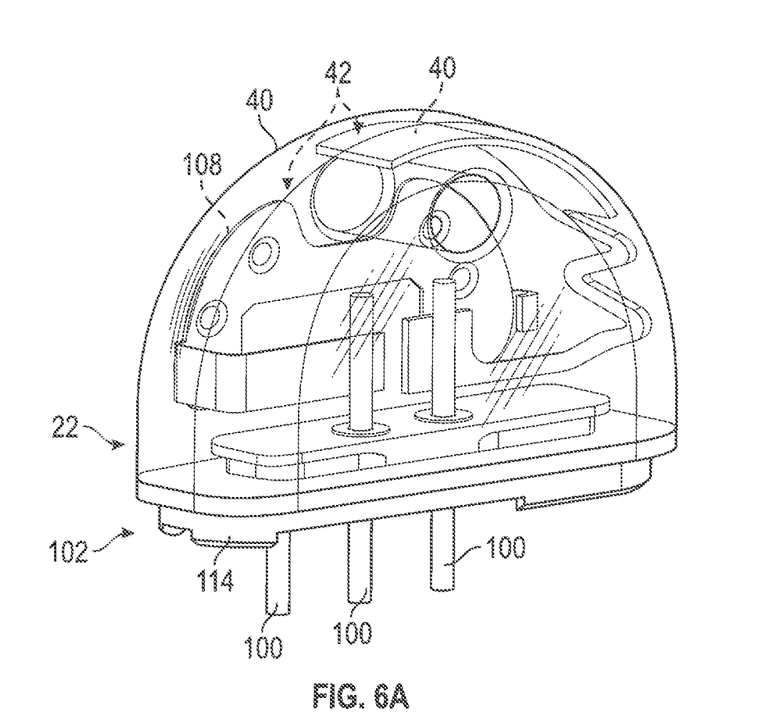
FIGS. 6A-6E are isometric views of a modular header-feedthru assembly incorporating the header assembly of an ICM along with a feedthru.
Figure 6B:
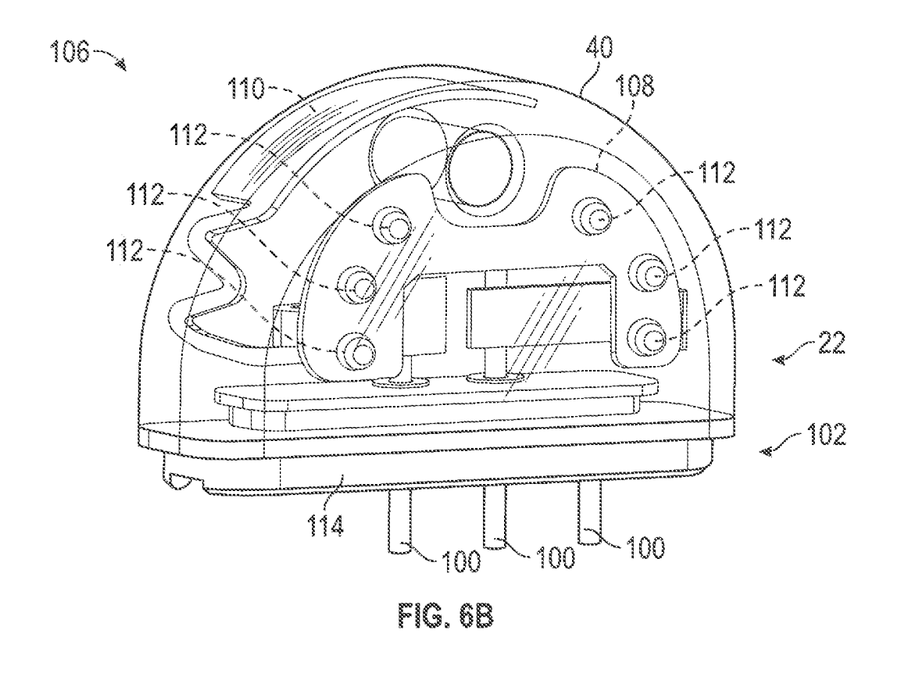
Figure 6C:
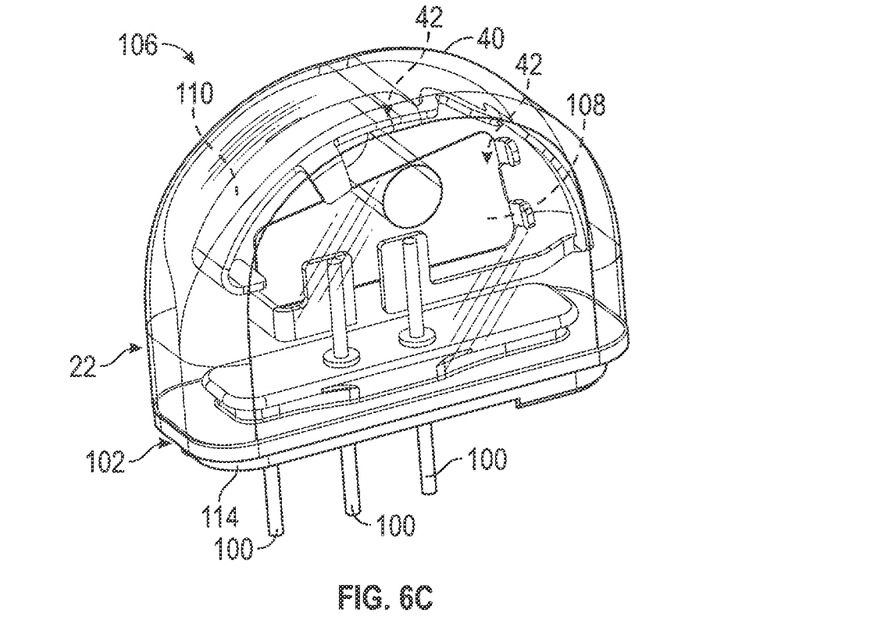
Figure 6D:
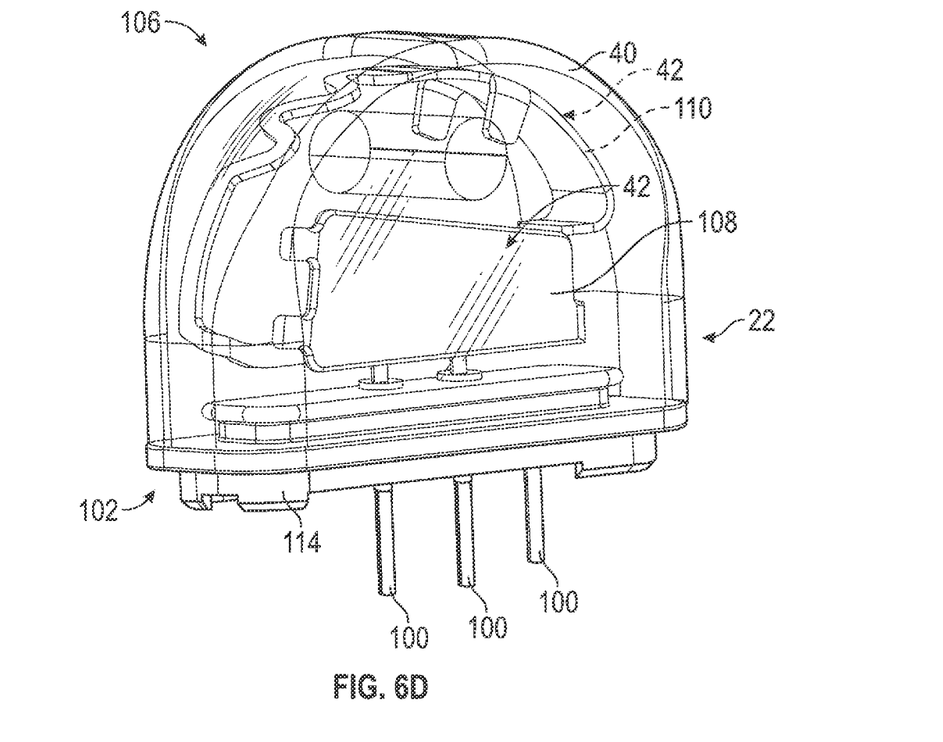
Figure 6E:
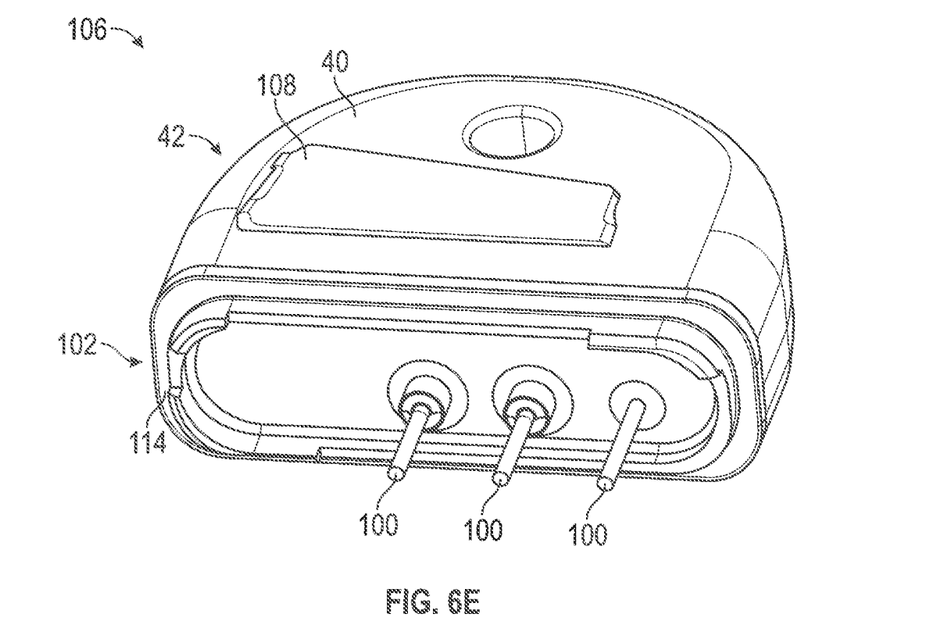

As illustrated in FIGS. 6A and 6B, the electrode plate 108 may include multiple electrodes 112, which may be in the form of outwardly projecting hemispherical bumps or oppositely configured hemispherical recesses. As indicated in FIGS. 6C-6E, the electrode plate 108 may simply have a generally continuous flat outer surface. The electrode plate, BLE antenna, and feedthru terminals 100 may be formed from a variety of biocompatible, electrically conductive metals, such as, for example, stainless steel, platinum, platinum-iridium alloy, MP35N, or etc.

As can be understood from FIGS. 6A and 6B, with the exception of the electrodes 112 and the surrounding side of the electrode plate 108, which are fully exposed, both the interior side and side edges of the electrode plate 108 and the BLE antenna 110 are fully encased in the header 40, which is in the form of a polymer material injected molded about the interior side and edges of the electrode plate and the BLE antenna, as discussed in greater detail below. Similarly, as can be understood from FIGS. 6C-6E, with the exception of the fully exposed generally continuous flat outer surface of the electrode plate 108, both the rest of the electrode plate 108 and the BLE antenna 110 are fully encased in the header 40. The header 40 is also injected molded onto the feedthru 102, as discussed in greater detail below, thereby coupling the header 40 to the feedthru and forming the modular header-feedthru assembly 106 of FIGS. 6A-6E.

As discussed in detail below, once the header assembly 22 is completed such that the header 40 is injected molded about the electrically conductive components (e.g., in the case of an ICM 20, the electrically conductive components of the conductor assembly 42) and to the feedthru 102 to form a resulting modular header-feedthru assembly 106, the feedthru terminals 100 are plugged into electrical receptacles 104 located in the housing 24 of the IPG 20 similar to that discussed below with respect to FIGS. 10 and 11. As a result, the feedthru terminals 100 extend from circuitry of the ICM 20 contained in the housing 24 of the ICM 20 to the electrically conductive components of the connector assembly 42.

As can be understood from the preceding discussion and as provided in greater detail below, the header-feedthru assembly 106 forms a first module that is plugged into electrical receptacles 104 of the housing 24, which forms a second module. The feedthru 102 of the header-feedthru assembly 106 is welded to the housing 24 to complete the assembly of the ICM 20 as it generally appears in FIG. 5.

C. Modular Header-Feedthru Assembly, Its Manufacture and Joining to an IED Housing To begin a discussion of the manufacture of the modular header-feedthru assembly 106 discussed above and its combination with a housing 24 to form an IED 20 that is either an IPG 20 (see FIG. 2) or an ICM 20 (see FIG. 5). reference is made to FIG. 7, which is flow chart outlining the manufacturing method, and to FIGS. 8A and 8B, which are opposite isometric views of the conductor assembly 42 and the feedthru 102 of the modular header-feedthru assembly 106 of FIGS. 6A and 6B. As shown in FIGS, 8A and 8B, the electrode plate 108 and the BLE antenna 110 are each welded or otherwise electrically connected to the respective terminals 100 of the feedthru 102 [block 200]. As can be understood from FIGS. 6A-6E, the polymer material of the header 40 is direct injected molded about the conductor assembly 42 and the upper portion of the base 114 of the feedthru 102 to form the modular header-feedthru assembly 106 [block 210]. In one embodiment, the polymer material is a biocompatible thermoplastic material such as, for example, Tecothane, Pallathane, Polycarbonate, Polyurethane, or etc.

Figure 9A:
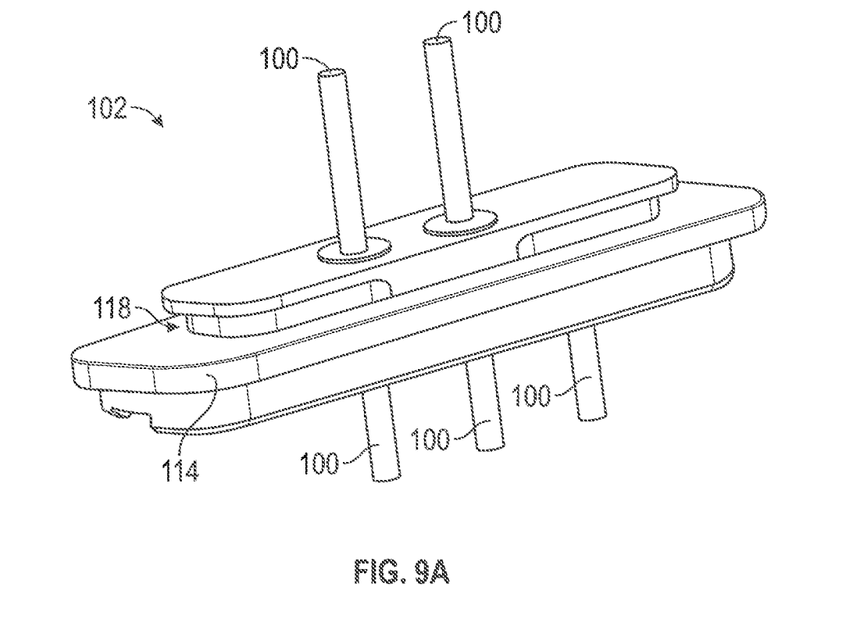
FIGS. 9A and 9B are, respectively, isometric and side elevation views of the feedthru 102.
Figure 9B:
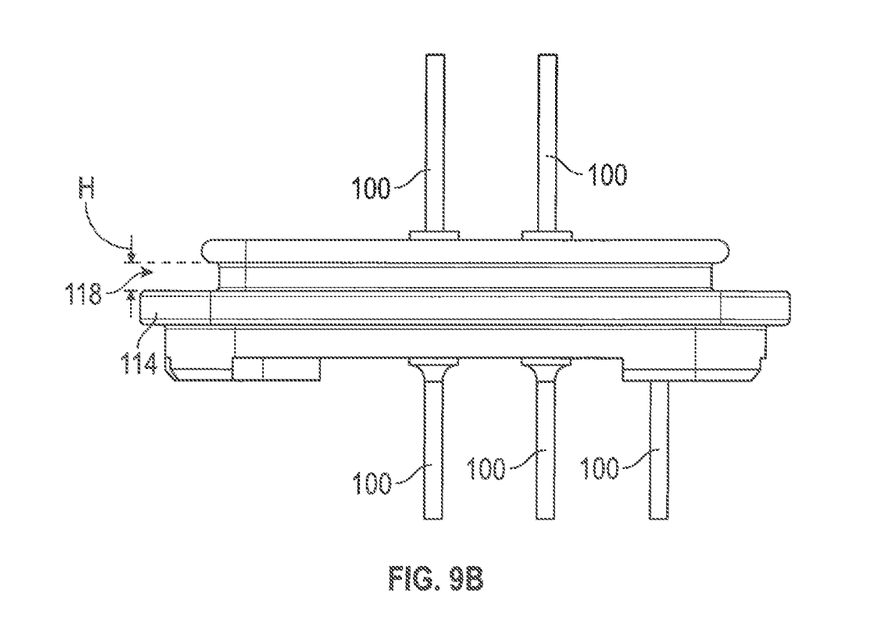

As can be understood from FIGS. 6A-6E, and also from FIGS. 9A and 9B, which are, respectively, isometric and side elevation views of the feedthru 102, the feedthru 102 includes a groove 118 defined in the base 114 of the feedthru 102, and the polymer material of the header 40 fully occupies the groove 118, thereby securing or anchoring the header 40 to the feedthru 102 upon the polymer material of the header having been injected about the conductor assembly 42 and the feedthru base 114 and curing thereabout. In one embodiment, the groove 118 extends in a recessed manner horizontally and circumferentially about the base 118 to form a substantial recess that the polymer material resides in anchoring the header 40 to the feedthru base 114. As illustrated in FIG. 9B, the groove 118 has a recess depth D of between approximately 0.01" and approximately 0.03", and a recess height H of between approximately 0.01" and approximately 0.03".

Figure 10:
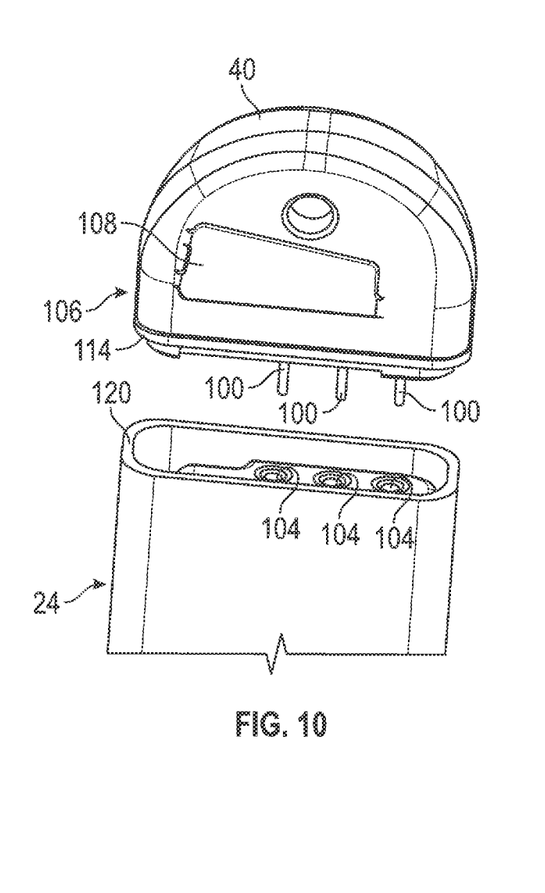
FIG. 10 is an isometric view of the modular header-feedthru assembly being aligned with the mating end of the device housing.

As illustrated in FIG. 10, which is an isometric view of the modular header-feedthru assembly 106 being aligned with the mating end of the device housing 24 [block 220], the housing 24 includes multiple female electrical receptacles 104 that are of a size, configuration, spacing and number to receive in a male-female arrangement the male feedthru terminals 100 of the modular header-feedthru assembly 106. The device housing 24 includes an upper edge 120 that extends around the receptacles 104.

Figure 11:
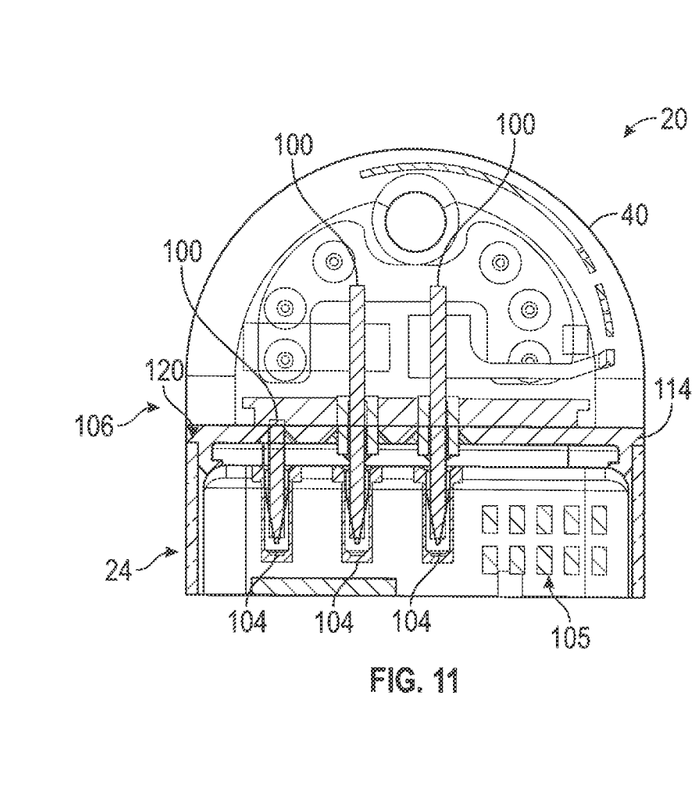
FIG. 11 is a longitudinal cross section of a header region of the completed ICM.

As can be understood from FIG. 11, which is a longitudinal cross section of a header region of the completed ICM 20, the modular header-feedthru assembly 106 is mated with the device housing 24 such that the male feedthru terminals 100 are fully received in the respective female electrical receptacles 104, and the bottom edge of the feedthru base 114 abuts against the upper edge 120 of the device housing 24 [block 230]. This receiving of the male feedthru terminals 100 within the respective female electrical receptacles 104 establishes a mechanical interference fit between the two types of electrically conductive structures 100, 104, thereby establishing an electrical connection between the electrical components of the modular header-feedthru assembly 106 and the electrical components of the device housing 24.

As can be understood from FIG. 11, the female electrical receptacles 104 may be supported by a hybrid 105 or other electronic components within, and supported by, the device housing 24. Thus, the female electrical receptacles 104 may be said to be operably coupled with the device housing 24.

Figure 12:
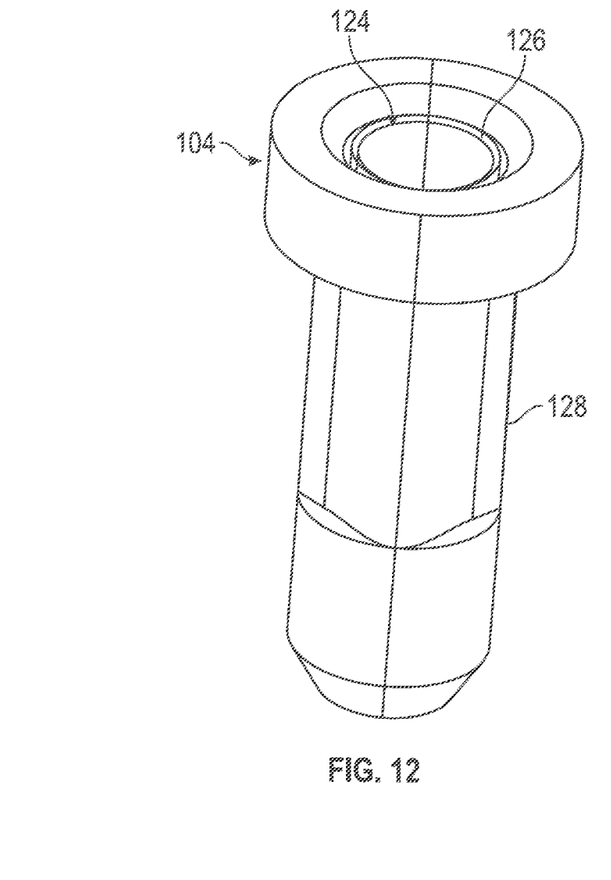
FIG. 12 is an isometric view of a female electrical receptacle.
Figure 13:
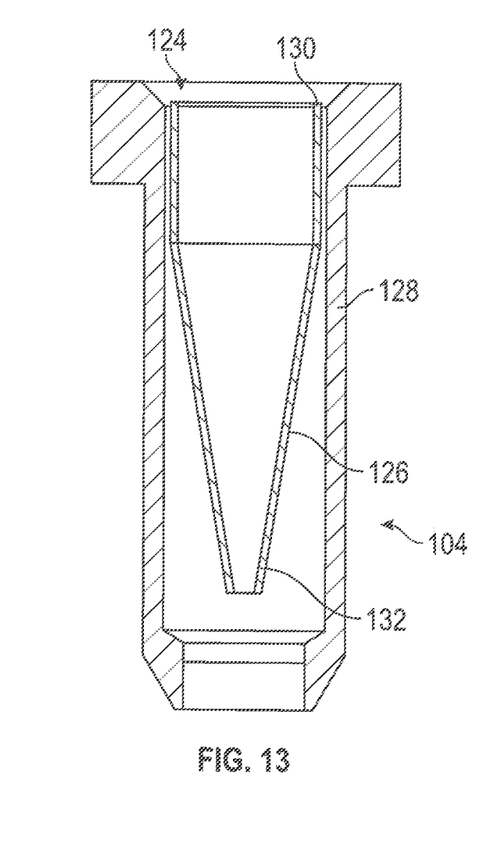
FIG. 13 is a longitudinal cross section of the female electrical receptacle.

As can be understood from FIG. 11 and FIG. 12, which is an isometric view of a female electrical receptacle 104, the receptacle 104 has a cylindrical hole 124 that has a diameter and shape that corresponds to the cylindrical outer surface of a feedthru terminal 100 received in the receptacle 104. As indicated in FIG. 13, which is a longitudinal cross section of the female electrical receptacle 104, the receptacle 104 includes a biasing member 126 located within the confines of an outer shell 128. The interior of the biasing member 126 defines the cylindrical hole 124.

As shown in FIG. 13, in one embodiment, the biasing member 126 takes the form of a downward tapering funnel with an inner diameter at its top 130 that is slightly larger than the outer diameter of the feedthru terminal 100 to be received in the biasing member 126. The inner diameter of the biasing member 126 decreases at a steady rate moving towards the narrow bottom end 132 of the biasing member 126. The funnel portion of the biasing member 126 is longitudinally segmented in at least one or more locations about its circumference to facilitate the funnel portion expanding to receive a feedthru terminal 100 in an interference fit wherein the funnel portion biases against the outer circumferential surface of the feedthru terminal 100. Since the biasing member 12$ is in electrical contact with the outer shell 128, which is in electrical communication with the electrical components of the device housing 24, and the biasing member 126 is in electrical contact with the feedthru terminal 100 received in the biasing member 126, the feedthru terminal being in electrical communication with the electrical components of the modular header-feedthru assembly 106, electrical communication is established between the electrical components of the modular header-feedthru assembly and the electrical components of the device housing.

In other embodiments, the biasing member 126 make take other forms such as, for example, a linearly extending spring-like member extending the length of the interior of the outer shell 128. The outer shell and the biasing member may be made from a variety of electrically conductive metals such as, stainless steel, platinum, platinum-iridium alloy, gold, beryllium copper, or etc.

Figure 7:
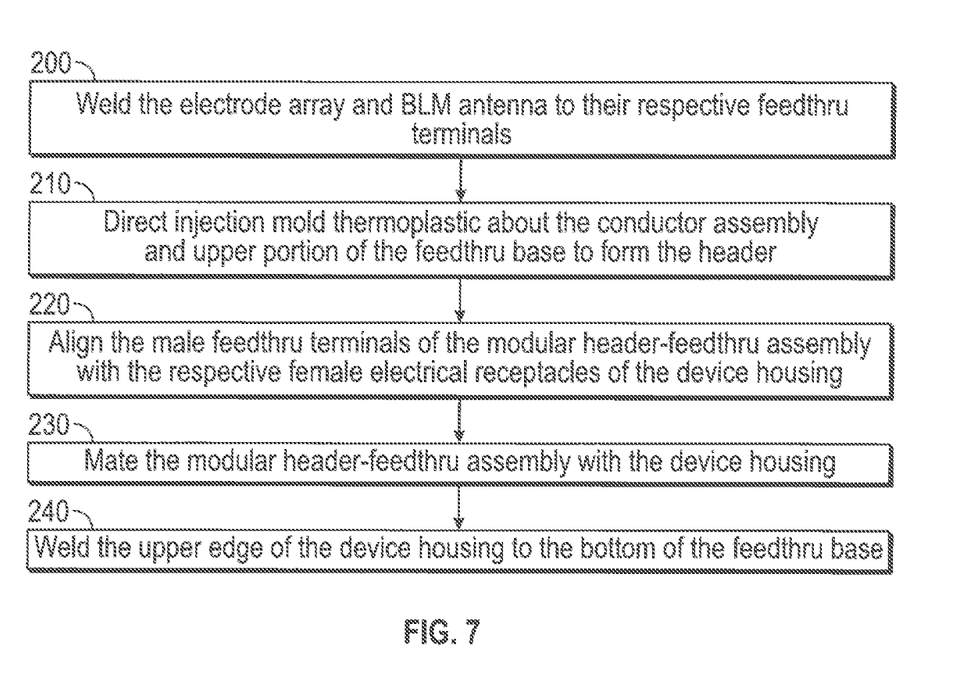
FIG. 7 is flow chart outlining a method of manufacturing any of the implantable electronic devices disclosed herein.
Figure 8A:
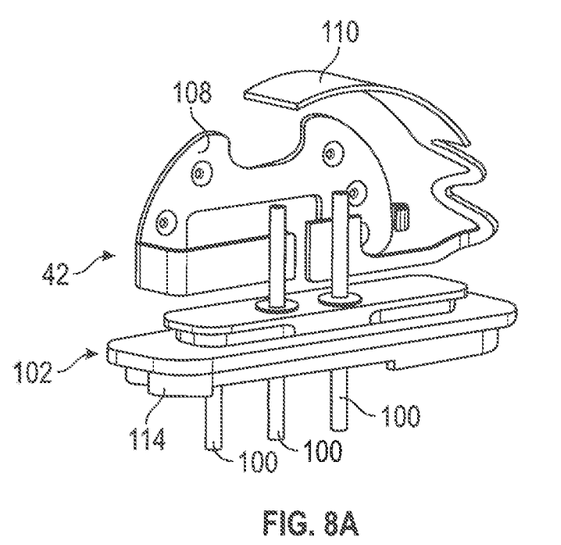
FIGS. 8A and 8B are opposite isometric views of the conductor assembly and the feedthru of the modular header-feedthru assembly of FIGS. 6A and 6B.
Figure 8B:
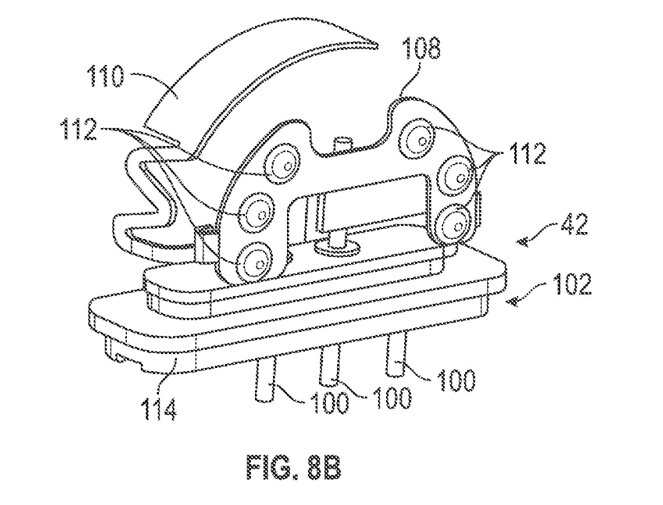

As can be understood from FIGS. 7 and 11, once the feedthru based 114 is mated with the top of the device housing 24 and the feedthru terminals 100 are plugged into the receptacles 104, the upper edge 120 of the device housing 24 is welded to the bottom or flange portion of the feedthru base 114 to form a hermetically sealed junction between the modular header-feedthru assembly 106 and the device housing 24 [block 240]. The ICM 20 is now complete and, as a result, the feedthru terminals 102 extend from circuitry of the ICM 20 contained in the housing 24 of the ICM 20 to the electrically conductive components of the connector assembly 42 encased by the injected polymer of the header 40.

The above described IPG 20 and ICM 20 are advantageous in that they have a robust configuration that has less associated manufacturing costs than those devices known in the art. The above-described manufacturing method facilitates an advantageous modular assembly of an IED 20 that is able to take advantage of direct injection molding for the manufacture of a modular header-feedthru assembly 106, which can then be plugged into the device housing 24 and welded thereto.

The foregoing merely illustrates the principles of the invention, Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. An implantable electronic device comprising:
   a modular header-feedthru assembly comprising:
      a conductor assembly;
      a feedthru base;
      a feedthru terminal coupled to and extending through the feedthru base, the feedthru terminal electrically coupled to the conductor assembly; and
      a polymer header molded about a portion of the feedthru base,
   wherein the modular header-feedthru assembly forms a unitary assembly in which the conductor assembly is at least partially contained within the polymer header and the feedthru terminal extends out of the polymer header through the feedthru base; and
   a housing defining a recess, the housing further containing,
   a female electrical receptacle within the recess and electrically coupled to internal electronic components of the housing,
   wherein the housing includes a mating end with a cavity that receives the modular header-feedthru assembly such that the housing is coupled to the feedthru base, the cavity configured to align the feedthru terminal with the female electrical receptacle as the modular header-feedthru assembly is inserted into the cavity, the feedthru terminal received within the female electrical receptacle to electrically couple the conductor assembly to the internal electronic components of the housing.

2. The implantable electronic device of claim 1, wherein an upper edge of the housing at the mating end is coupled to the feedthru base by a weld and the weld forms a hermetic seal between the upper edge of the housing and the feedthru base.

3. The implantable electronic device of claim 1, wherein the female electrical receptacle comprises a biasing member that biases against the feedthru terminal.

4. The implantable electronic device of claim 3, wherein the biasing member comprises a funnel portion.

5. The implantable electronic device of claim 1, wherein the polymer header comprises a thermoplastic.

6. The implantable electronic device of claim 1, wherein the conductor assembly comprises an electrode plate and a Bluetooth Low Energy (BLE) antenna.

7. The implantable electronic device of claim 6, wherein the electrode plate comprises an electrode surface in the form of a generally continuous flat surface.

8. The implantable electronic device of claim 6, wherein the electrode plate comprises an electrode surface having at least one of bumps or recesses.

9. The implantable electronic device of claim 1, wherein the implantable electronic device is an implantable pulse generator and wherein the conductor assembly is in the form of a connector assembly having at least one of a ring block, a tip block, or an antenna.

10. The implantable electronic device of claim 1, wherein the feedthru base comprises a groove and the polymer header fully occupies the groove to anchor the polymer header to the feedthru base.

11. The implantable electronic device of claim 10, wherein the groove extends in a recessed manner horizontally and circumferentially about the feedthru base.

12. The implantable electronic device of claim 11, wherein the groove has a recess depth of between approximately 0.01" and approximately 0.03", and a recess height of between approximately 0.01" and approximately 0.03".

13. The implantable electronic device of claim 1, wherein the housing contains a hybrid within the recess, and the hybrid supports the female electrical receptable within the recess.

14. The implantable electronic device of claim 1, wherein the cavity is defined by an upper edge of the housing at the mating end, the upper edge having a closed shape.

15. A method of manufacturing an implantable electronic device, the method comprising:
   direct injection molding a polymer material about a conductor assembly and an upper portion of a feedthru base to form a modular header-feedthru assembly, wherein the modular header-feedthru assembly comprises a feedthru terminal electrically coupled to the conductor assembly, the feedthru terminal extending through the feedthru base and projecting from a bottom portion of the feedthru base;
   loading the modular header-feedthru assembly into a cavity at a mating end of a housing of the implantable electronic device to mate the bottom portion of the feedthru base with the mating end of the housing, the housing containing a female electrical receptacle electrically connected to internal electronic components within the housing, wherein the cavity is configured to align the feedthru terminal with the female electrical receptacle as the modular header-feedthru assembly is loaded into the cavity, the feedthru terminal received within the female electrical receptacle to electrically couple the conductor assembly to the internal electronic components within the housing; and
   welding the bottom portion of the feedthru base to the mating end of the housing.

16. The method of claim 15, wherein the housing is operably coupled with at least one of a battery or a hybrid.

17. The method of claim 15, wherein the welding between the mating end of the housing and the bottom portion of the feedthru base forms a hermetic seal between the housing and the feedthru base.

18. The method of claim 15, wherein the polymer material comprises a thermoplastic.

19. The method of claim 15, wherein the implantable electronic device is an implantable cardiac monitor and wherein the conductor assembly comprises an electrode plate and a BLE antenna.

20. The method of claim 15, wherein the implantable electronic device is an implantable pulse generator and wherein the conductor assembly is in the form of a connector assembly comprising at least one of a ring block, a tip block, or an antenna.

21. The method of claim 15, wherein the feedthru base comprises a groove and the polymer material is caused to fully occupy the groove in anchoring the polymer material to the feedthru base.

22. The method of claim 21, wherein the groove extends in a recessed manner horizontally and circumferentially about the feedthru base.

* * * * *